United States Patent [19]

Della Sala

[11] Patent Number: 4,869,656

[45] Date of Patent: Sep. 26, 1989

[54] FERROMAGNETIC-FLUID PUMP FOR PUMPING BIOLOGICAL LIQUID

[76] Inventor: Berardino Della Sala, Via Ticino, 1, 21021 Angera, Varese, Italy

[21] Appl. No.: 122,933

[22] Filed: Nov. 19, 1987

[30] Foreign Application Priority Data

Dec. 23, 1986 [IT] Italy ............................ 22858 A/86

[51] Int. Cl.$^4$ ............................................. F04B 43/00
[52] U.S. Cl. ......................................... 417/412; 623/3
[58] Field of Search ................. 417/50, 481, 43, 97, 417/103, 436, 412, 413; 627/3

[56] References Cited

U.S. PATENT DOCUMENTS

| | | | |
|---|---|---|---|
| 3,511,583 | 5/1970 | Brown | 623/3 |
| 3,633,217 | 1/1972 | Lance | 417/50 |
| 3,720,485 | 3/1973 | Hulman | 623/3 |
| 3,733,616 | 5/1973 | Willis | 623/3 |
| 3,768,931 | 10/1973 | Willis | 417/412 |
| 3,874,002 | 4/1975 | Kurpanek | 417/50 |
| 4,058,857 | 11/1977 | Runge | 623/3 |
| 4,063,826 | 12/1977 | Riepe | 417/436 |
| 4,375,941 | 3/1983 | Child | 623/3 |
| 4,650,485 | 3/1987 | Della Sala | 623/3 |

FOREIGN PATENT DOCUMENTS

| | | | |
|---|---|---|---|
| 0132081 | 7/1985 | Japan | 417/412 |
| 0931959 | 5/1982 | U.S.S.R. | 417/412 |

Primary Examiner—Richard J. Apley
Assistant Examiner—James Prizant
Attorney, Agent, or Firm—Ladas & Parry

[57] ABSTRACT

A ferromagnetic-fluid pump includes a hollow body having a substantially rigid structure and an internal diaphragm dividing said body in two cavities. Each cavity has an inlet and an outlet opening provided with one-way valve. One edge of said diaphragm is hinged on the body structure while its opposite edge is spaced from the adjacent inner surface of said body. Said cavities are partially filled with a ferromagnetic fluid which seals said diaphragm in respect of the inner surface of said body. At least one electric winding is provided onto both sides of said diaphragm and onto the two inner surfaces of said body facing said diaphragm. Said windings are operative to generate a variable magnetic fluid so that said diaphragm oscillates.

6 Claims, 2 Drawing Sheets

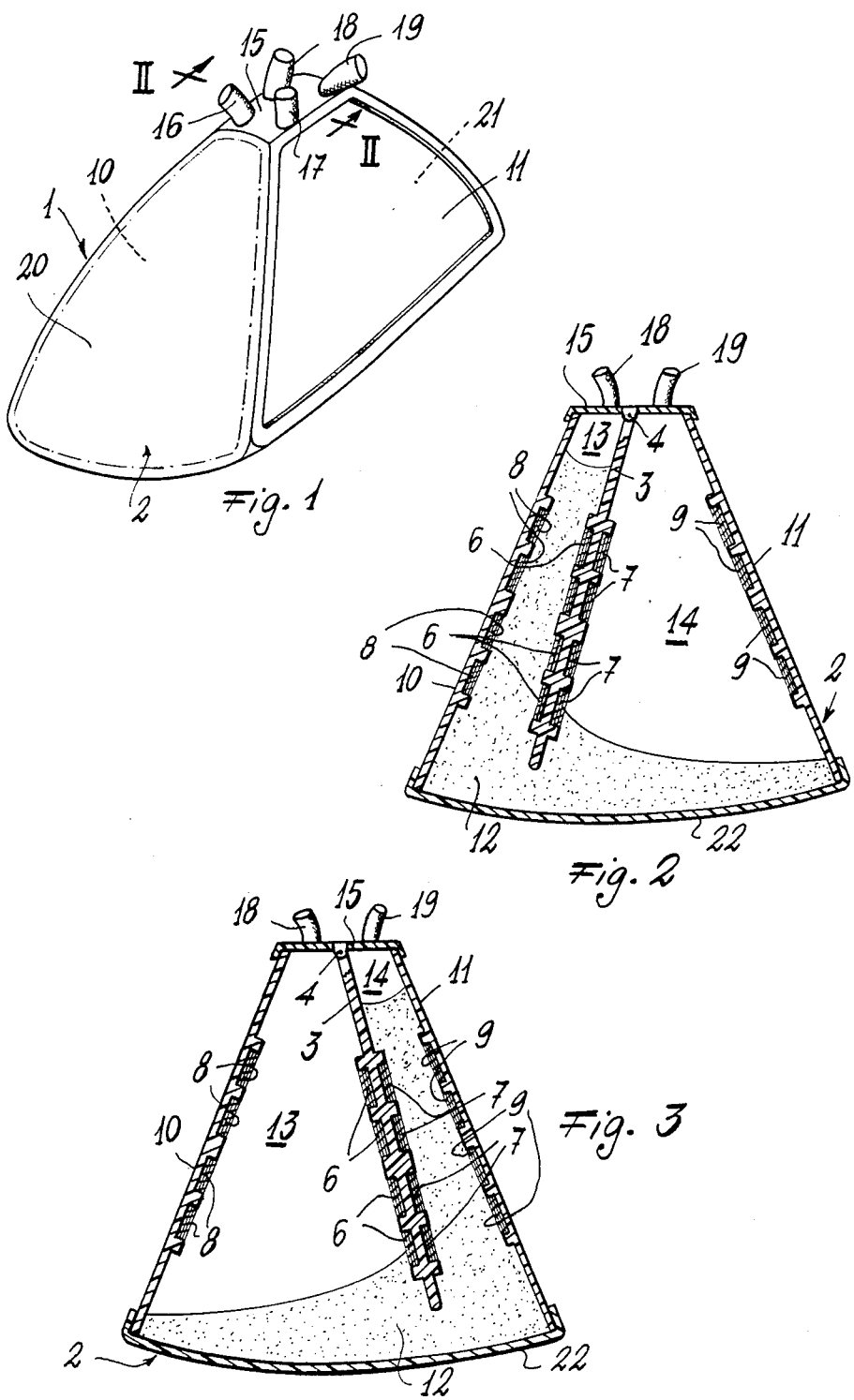

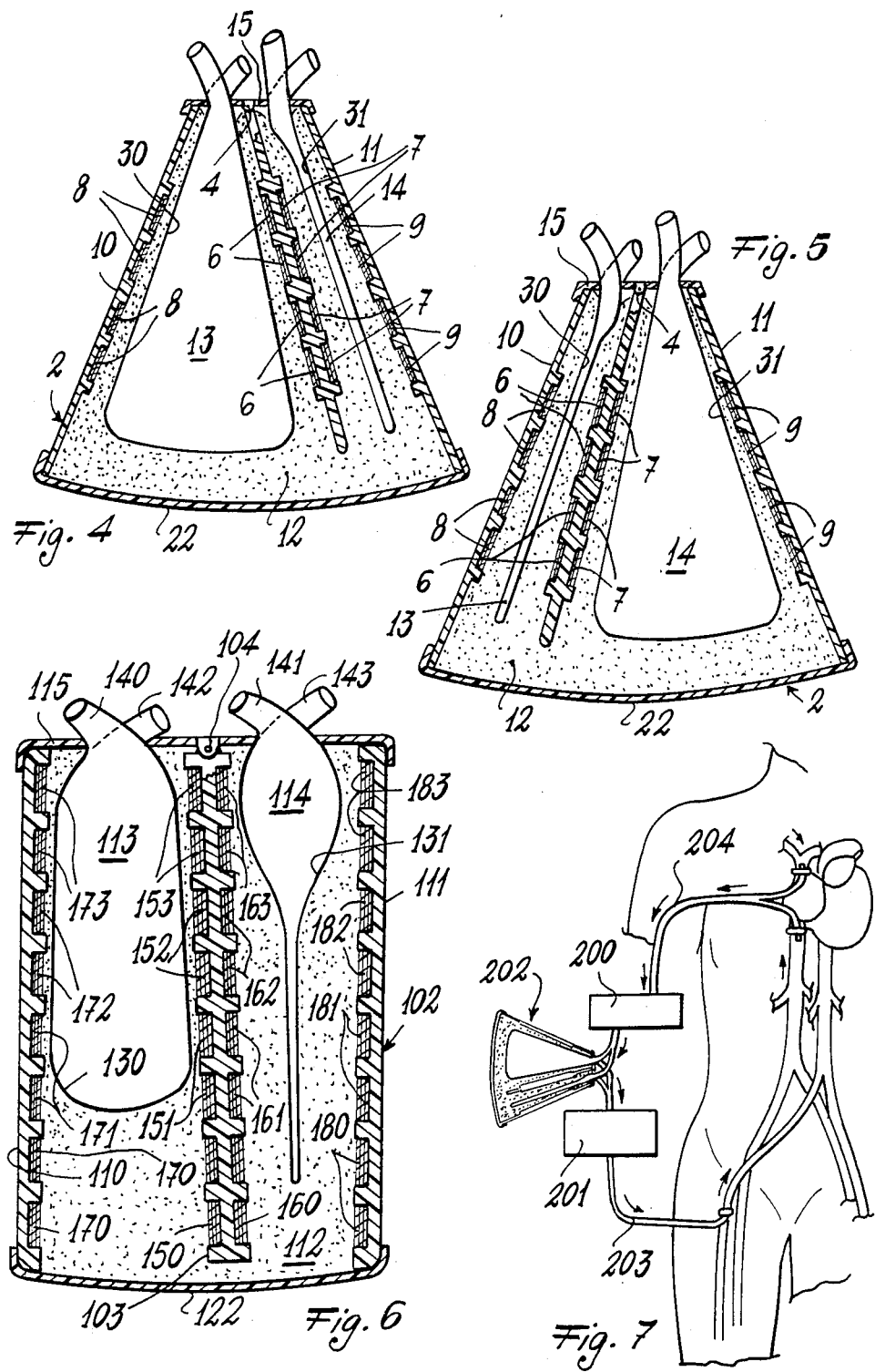

FERROMAGNETIC-FLUID PUMP FOR PUMPING BIOLOGICAL LIQUID

This invention relates to a pump for biological fluids, more particularly a ferromagnetic-fluid pump. Artificial hearts, known in the medical field, are in fact pumps for pumping blood.

FR-A-No. 2,485,928 discloses an artificial heart having a hollow, elastomeric body whose external walls incorporate a magnetic substance. An intermediate wall or diaphragm divides the internal room of said body in two independent cavitites. Said diaphragm incorporates some electric windings so that a magnetic field is generated as said windings are connected to an external d.c. power source. As a consequence, the external walls are attracted towards the diaphragm, thereby expelling through relevant valves the blood contained within said body.

This type of artificial heart has the following shortcomings: very low efficiency; external wall having ag reat displacement which causes mechanical damages to the adjacent organs of the human body; ad a too quick movement of said walls as the windings are energized, so that the pumping action causes mechanical damages to the blood.

US-A-No. 3,768,931 discloses a magnetically actuated pump usuable as an artificial heart which minimizes the mechanically induced damage both to the blood and to the surrounding organs. In fact the pump has a rigid, external shell containing a plurality of electromagnets. A flexible bag is contained within said rigid shell. A plurality of magnetic poles, oriented in a predetermined pattern, are affixed to the outer surface of said flexible bag.

Assuming that when the elecromagnets are energized by a current flow in one direction that magnets will be repelled from the electromagnets, it shall happen that when the electromagnets are energized in the reverse direction the magnets will be attracted to the electromagnets. Therefore, the flexible bag can be alternatively compressed or expanded, thereby producing a pumping effect. Suitable valves allow the blood to enter the bag and be expelled therefrom. This artificial heart does not suffer the shortcomings of the preceding case, however the internal flexible bag has too short a life due to the presence of magnets on its outer surface.

In US-A-No. 3,551,583 a pump actuated by means of a ferromagnetic fluid is disclosed. As known (see also Transaction on Magnetics, IEEE Magnetics Society, March 1980, volume MAG-16, No. 2) a ferromagnetic fluid is a colloidal suspension of micro-sized particles of a magnetizable material such as ferrite or rare earths, in a carrier fluid such as kerosene, with a dispersing agent such as an oleic acid coating on the particles to prevent flocculation. As known (see paper "Medical Application of Magnetic Fluids" by P.D.S. Verma, in Acta of Second International Conference on Physiological Fluiddynamics, Madras (India) August 10–12, 1987), ferromagnetic fluids are used in the medical field, particularly in radio diagnosis as contrast media.

The electromagnetic pump comprises a rigid hollow body having two openings. A flexible duct passes through said hollow body and said openings. A ferromagnetics fluid is contained between said hollow body and said duct. Sealing means are provided between said openings and said duct. Means for periodically establishing a magnetic field along the axial portion of said duct are provided in order to attract said ferromagnetic fluids towards said periodically collapsing duct. Therefore, a liquid contained in said duct is pumped, axially to the duct, in one of the two directions. However, the power of such a type of pump is too low to be used as an artificial heart. Moreover, the pressure in the blood still varies too quickly.

A type of pump for biological liquids actuated by means of an electromagnetic field and a ferromagnetic fluid is that disclosed in US-A-No. 4,650,485 whose inventor is the same as that of the present application. In this patent two fundamental kinds of pump are illustrated. The pumps in FIGS. 1–11 have a substantially rigid housing, while the pumps illustrated in FIGS. 12–16 have a variable-volume housing. The pumps of the first kind have an internal flexible diaphragm consisting of two flexible membranes entrapping a ferromagnetic fluid. It was found that, also in this case, the pressure within the blood varies too quickly, causing mechanical damage to the blood. The pumps of the second kind (FIGS. 12–16) having a variable-volume housing, have the aforementioned shortcoming, i.e. mechanical damages to the adjacent organs can occur.

It is the aim of this invention to provide a ferromagnetic-fluid pump for biological liquids, which can obviate the shortcomings and deficiencies of the prior pumps of such a type.

The ferromagnetic fluid-pump, particularly one for pumping biological liquids, according to the present invention includes:

a hollow body having an internal diaphragm dividing said hollow body in two cavities, each of said cavities having an inlet and an outlet opening provided with a one-way valve;

a ferromagnetic fluid partially filling said cavity;

at least one electric winding provided onto both the sides of said diaphragm and onto the two inner surfaces of said hollow body facing said diaphragm, said windings being operative to generate a variable magnetic field; characterized in that:

said hollow body has a substantially rigid structure;

one edge of said diaphragm is connected to the hollow body structure by means of a pin upon which said diaphragm is hinged and oscillable;

the opposite edge of said diaphragm is spaced from the adjacent, inner surface of said hollow body;

said ferromagnetic fluid seals said diaphragm in respect of the inner surface of said hollow body and defines, together with said hollow body and diaphragm, two pumping chambers communicating with said inlet and outlet openings.

The substantially rigid structure of the pump according to the present invention prevents any mechanical damages to the adjacent organs and, moreover, the operating mode of said pump provides for a gradual variation of the pressure into the biological liquid, so that no mechanical damage to the blood occurs.

Therefore, the two main shortcomings of the prior art pumps are simultaneously eliminated. The pump of the present invention, due to its reduced size and high reliability, can be used as a total artificial heart to be accomodated within the thorax in the place of the heart to be replaced. Obviously, the pump can be also used in hemodialysis apparatus or as artificial heart in an extracorporeal circulation system during open heart operations. A pump according to the invention may besides have many other applications, such as an artificial pancreas, a urinary cyst, or a device for administration of pharmaceutical products, as disclosed hereinafter. Due to its very reduced size, the pump can be accomodated within the subcutaneus fatty tissue areas.

In one embodiment of the pump according to the invention each of said pumping chambers is defined by a flexible bag which separates the volume of the relevant chamber from said ferromagnetic fluid.

In another embodiment of the pump a set of windings is provided onto both sides of said diaphragm and onto both of the inner surfaces of said hollow body facing said graphragm; said windings in each set of windings being stepwise energized, from the farthest to the nearest in respect of said pin upon which said diaphragm is oscillable. A control means, such as a microprocessor, controls the stepwise energization of said windings of the relevant set of windings. Said control means also controls the value of the intensity of electric current flowing through said windings and the period of energization.

Where the pump according to the invention is used as an artificial heart, a portion of said hollow body is elastically deformable to a certain extent under the action of inner pressure so hat the volume of said hollow body varies as a function of the inherent variability of venous blood input to heart. Preferably, said elastically deformable portion of the hollow body is normally the bottom wall thereof. Obviously, the variation of the volume of said hollow body is very small with respect to the volume thereof.

Further features, advantages and details of the ferromagnetic-fluid pump according to the invention will be more readily apparent from the following description, with reference to the accompanying drawings illustrating some exemplary and not lilmitative embodiments thereof, and where:

FIG. 1 shows a perspective view of the first embodiment of the pump according to the invention;

FIG. 2 is a diagrammatic cross-sectional view along line II—II in FIG. 1, wherein the diaphragm is completely deflected in one direction;

FIG. 3 is a cross-sectional view similar to FIG. 2, with the only difference that the diaphragm is completely deflected in the opposite direction;

FIGS. 4 and 5 show a cross-sectional view, similar to that of FIGS. 1 and 2, of another embodiment of the pump having two flexible bags separating ferromagnetic fluid from biological liquid to be pumped;

FIG. 6 shows a cross-sectional view of a further embodiment of the invention wherein the deflection of the diaphragm is very small; and FIG. 7 illustrates a utilization of the pump in an extracorporeal circulation system, said system being used in an open heart operation.

With reference to FIGS. 1, 2 and 3 the pump according to the invention is generally indicated at 1. Said pump includes a hollow body 2 generally having an approximatively pyramidal shape. Said hollow body 2 includes two substantially flat side walls 10, 11, substantially flat front and rear walls 20, 21, an arcuated bottom wall 22, and a top wall 15. An inner oscillating diaphragm 3 divides the inner volume of said hollow body 2 in two portions whose volume varies between a minimum and maximum value during the oscillation of said diaphragm 3. The latter is hinged at 4 to the top wall 15 of said hollowo body 2 and bears two couples of windings (6 and 7), one on each of its sides. A couple of windings 8 and a couple of windings 9 are provided onto each of the inner surfaces of the side walls 10 and 11 respectively, facing said diaphragm 3. Said windings 6, 7, 8 and 9 generate a magnetic field as an electric current supplied by a d.c. power source (not shown) flows through them.

A ferromagnetic fluid 12 partially fills said hollow body 2, the remaining space within it forming two chambers 13 and 14, one on each side of said diaphragm 3. Said chambers 13 and 14 have a volume which is cyclically variable between a minimum and a maximum value due to the oscillation of said diaphragm 3 (see FIGS. 2 and 3). An inlet and an outlet valve is provided in the top wall 15 on each side of said diaphragm 3. Said valves communicate with relevant inlet (16, 17) or outlet (18, 19) ducts respectively. The bottom wall 22 of said hollow body 2 has an arcuated profile so that the pump has a minimum volume. Where the pump is used as an artificial heart, said bottom wall 22 has a certain compliance, i.e. it is elastically deformable to a certain extent under the action of pressure within the pump. Therefore, the volume of said chamber 13 and 14 varies as a function of the inherent variability of venous blood input to heart. Obviously, any of the other walls may be elastically deformable in place of or in addition to said bottom wall.

Operating said pump 1 is very simple. In order to produce the cyclic oscillation of said diaphragm 3, all the windings on one side of said diaphragm 3 (e.g. 6 and 8) are energized by electrically connecting said windings with the d.c. power source (not shown) through a switch controlled by a control means (not shown). A magnetic field is established, so that said diaphragm 3 oscillates towards the left. Before said diaphragm 3 reaches its maximum deflection (FIG. 2) said control means disconnects windings 6 and 8, and connects windings 7 and 9 on the other side of said diaphragm 3. Therefore, a magnetic field is established which slows the oscillation of said diaphragm 3 towards the left, until it stops and then reverses its motion. In the same way, a subsequent reversion of the movement of said diaphragm 3 is obtained. Therefore, by said control means, it is possible to control the oscillation deflection of said diaphragm 3. Said control means is also able to control the intensity of the magnetic field, so that it is possible to control the oscillation period of said diaphragm 3.

It should be noted that the ferromagnetic fluid 12 also acts as a sealing means between the chambers 13 and 14, and at the same time defines the bottom of said chambers 13 and 14. The presence of a magnetic field prevents the feromagnetic fluid 12 from abandoning the region where the magnetic field is established, so that ferromagnetic fluid 12 cannot leave said hollow body 2 through the outlet openings.

As well know to a person skilled in the art, suitable kinds of ferromagnetic fluid are non-miscible and compatible with biological liquids.

FIGS. 4 and 5 show a second embodiment of the pump according to the invention, wherein the chambers 13 and 14 are defined by flexible bags 30, 31. This embodiment can be useful when a complete separation between ferromagnetic fluid andn biological liquid is required. For the rest this embodiment is the same as that of FIGS. 2 and 3.

A further embodiment of the pump according to the invention is shown in FIG. 6. In it diaphragm 103 is hinged at 104 to the top wall 115. However, the displacement of said diaphragm 103 during its oscillation is very small in comparison with the two previously disclosed embodiments. In the present embodiment the hollowo body 102 generally has a parallelepiped shape and includes two side walls 110 and 111, a bottom wall 122, a top wall 115, and a front and a rear wall (not shown). Both the sides of said diaphragm 103 bear a set of windings which individually, stepwise and upwardly, are energized. A correspondent set of windings is provided on the inner surface of both side walls 110 and 111. More particularly, windings 150–153 are provided on the left side of said diaphragm 103 and windings 160–163 on the right side thereof. Similarly, windings 170–173 and 180–183 are provided onto the inner surface of said walls 110 and 111 respectively.

Two flexible bags 130 and 131, one one ach side of said diaphragm 103, are provided as in the embodiment of FIGS. 4 and 5. A feromagnetic fluid 112 partially fills said hollow body 102. The stepwise and upwardly way of energizing the windings causes a little deflection of said diaphragm 103 and, simultaneously, the rising of said ferromagnetic fluid 112 along the walls onto which windings are stepwise energized (see FIG. 6, right portion). In this way a very gradual compression of the relevant flexible bag (131) is obtained, so that the pressure variation within the biological liquid contained into said bag is very gradual too. The pump of FIG. 6 is suitably controlled by a microprocessor providing for the stepwise energizing of the windings. Inle (140, 141) and outlet (142, 143) ducts are provided. Where the pump is not used as an artificial heart, inle ducts (140, 141) are merging in one duct and the same happens for the outlet ducts. Also in this case, a pump having a gradual variation of the pressure in the biological liquid is obtained.

As mentioned above, the pump according to the invention can be implanted within the human body as an artificial total heart which is further provided with a d.c. power source (a cell) and a microprocessor which controls the intensity of current flow through said windings and the period of energization thereof, i.e. the period of oscillation of said diaphragm.

Another application of the pump according to the invnetion is now illustrated with reference to FIG. 7. In it the pump is part of oan extracrporeal circulation apparatus used in an open heart operation. The extracorporeal circulation circuit includes an oxygenator 200 and a heat exchanger 201 (both schematically illustrated in FIG. 7). The pump 202 of the invention is inserted between said oxygenator 200 and heat exchanger 201. The latter is connected by means of duct 203 to the femoral arteria, while the oxygenator 200 is connected by duct 204 to both inferior and superior vena cava. The above illustrated apparatus is assisting the left ventricle of the patient's heart and may be completed by other known devices according to the particular needs. In this apparatus, pump 202 may have a cooling device and a thermostatic detector to maintain the biological liquid in the pump 202 at a predetermined temperature.

The pump of the invention is advantageously employed in combination with a hemodialysis apparatus, in place of the known pumps.

Other than as an artificial heart, the pump can be used in an artificial pancreas having the purpose to administer a monitored quantity of insulin. Said artificial pancreas essentially includes a bag containing a quantity of insuline, a pump according to the invention, a microprocessor for monitoring glycemia and controlling a d.c. power supply (a cell). The pump is inserted in a duct connecting said bag and a suitable vena, such as mesenterica superior. This apparatus is located under the skin in the abdomen area. Said bag is refilled by puncture through the skin.

Furthermore, a pump according to the invention may be used as an artificial urocyst replacing a surgically removed urocyst. In fact, urine can be collected in either chamber (13, 14; 113, 114) of said pump, and precisely in the chamber which offers the maximum volume at a given time (e.g. chamber 14 in FIG. 2), through the inlet duct (16, 17; 140, 141) until this chamber is full. By means of a sensor and of a control means (a microprocessor) the filled chamber can be emptied by energizing the relevant windings so that the diaphragm deflects. Obviously, in this case the movement of the diaphragm must be very slow and a high-density ferromagnetic fluid must accordingly be used. At the same time, the other chamber reaches its maximum volume, so that it is ready to collect urine. Then the cycle can be repeated.

A similar apparatus may be used for administering pharmaceutical products when necessary.

As to the material constituting the pump, hollow body and diaphragm are of well known plastic material of the kind compatible with biological liquid and human body. In the case in which bags are not provided, the kind of ferromagnetic fluid has to be selected according to the type of biological liquid to be pumped and windings are suitable coated with a plastic material compatible with the biological liquid.

Windings consist of a simple electroconductive wire, such as a copper wire, which generates a magnetic field as an electric current flows therethrough. Superconductive materials, at body temperature, would be particularly suitable when and if available on the market.

Actually, said ferromagnetic fluid acts itself as an electromagnetic core, so that the magnetic field is enhanced. Obviously, said windings could be the windings of relevant electromagnets.

As mentioned above, the pump according to the present invention is particularly suitable for pumping biological liquids. However, it could be obviously used for pumping any other liquid or gas, provided that the materials constituting the pump are compatible with said liquid or gas.

What I claim is:

1. A ferromagnetic-fluid pump, particulalry one for pumping biological liquids including:
   a hollow body having an internal diaphragm dividing said hollow body in two cavities, each of said cavities having an inlet and an outlet opening provided with a one-way valve;
   a feromagnetic fluid partially filling said cavity;
   at least one electric winding provided onto both the sides of said diaphragm and onto the two inner surfaces of said hollow body facing said diaphragm, said windings being operative to generate a variable magnetic field; wherein:
   said hollow body has a substantially rigid structure;
   one edge of said diaphragm is connected to the hollow body structure by means of a pi upon which said diaphragm is hinged and oscillable;
   the opposite edge of said diaphragm is spaced from the adjacent, inner surface of said hollow body; wherein said pump comprises two pumping chambers, one on either side of said diaphragm, each defined by a flexible bag which separates the volume of the relevant chamber from said ferromagnetic fluid.

2. The ferromagnetic-fluid pump according to claim 1, wherein a set of windings is provided on both sides of said diaphragm and on each of the inner surfaces of said hollow body facing said diaphragm, said windings in each set of windings being stepwise energized, from the farthest to the nearest in respect of said pin upon which said diaphragm is oscillable.

3. The ferromagnetic-fluid pump according to claim 2, wherein a microprocessor controls the stepwise energization of said windings of the relevant set of windings.

4. The ferromagnetic-fluid pump according to claim 2 wherein a microprocessor controls the intensity of the electric current flowing through said windings and the period of energization thereof.

5. The ferromagnetic-fluid pump according to claim 1, wherein a portion of said hollow body is to a certain extent elastically deformable outwardly under the action of the internal pressure.

6. The ferromagnetic-fluid pump according to claim 5, wherein said elastically deformable portion of the hollow body is the bottom wall thereof.

* * * * *